United States Patent [19]

Novick et al.

[11] Patent Number: 6,136,309
[45] Date of Patent: Oct. 24, 2000

[54] ANTIBODIES AGAINST THE INTERFERON (IFN) α/β RECEPTOR (IFNAR2) THAT PREFERENTIALLY BLOCK THE ACTIVITY OF IFN-α

[75] Inventors: Daniela Novick; Menachem Rubinstein, both of Rehovot, Israel

[73] Assignee: Yeda Research and Development Co. Ltd., Rehovot, Italy

[21] Appl. No.: 09/171,979

[22] PCT Filed: Apr. 29, 1998

[86] PCT No.: PCT/IL97/00138

§ 371 Date: Oct. 29, 1998

§ 102(e) Date: Oct. 29, 1998

[87] PCT Pub. No.: WO97/41229

PCT Pub. Date: Nov. 6, 1997

[30] Foreign Application Priority Data

May 1, 1996 [IL] Israel ........................................ 118096

[51] Int. Cl.[7] ........................ A61K 39/395; C07K 16/28; C12N 15/13; C12N 5/20
[52] U.S. Cl. ..................... 424/143.1; 424/133.1; 530/388.22; 530/387.3; 536/23.53; 435/320.1; 435/328; 435/334; 435/346; 435/7.24; 436/531
[58] Field of Search ............................ 530/388.22, 387.3; 536/23.53; 435/320.1, 328, 334, 346, 7.24, 69.6, 69.7; 436/531; 424/143.1, 133.1

[56] References Cited

FOREIGN PATENT DOCUMENTS

| | | |
|---|---|---|
| 0563487 | 10/1993 | European Pat. Off. . |
| 0588177 | 3/1994 | European Pat. Off. . |
| 0676413 | 10/1995 | European Pat. Off. . |
| 9507716 | 3/1995 | WIPO . |

OTHER PUBLICATIONS

Croze, E., et al. (1996). "The Human Type I Interferon Receptor." *J. Biol. Chem.* 271: 33165–68, Dec. 1996.

Platanias, L. C., et al. (1996). "Differences in Interferon α and β Signaling." *J. Biol. Chem.* 271: 23630–33, Sep. 1996.

Benoit, P., et al., "A Monoclonal Antibody to Recombinant Human IFN–α Receptor Inhibits Biologic Activity of Several Species of Human IFN–α, IFN–β, and IFN–[1], " *The Journal of Immunology* 150–3:707–716 (1993).

Colamonici, O.R., et al., "Identification of a Novel Subunit of the Type I Interferon Receptor Localized to Human Chromosome 21," *The Journal of Biological Chemistry* 268–15:10895–10899 (1993).

Novick, D., et al., "The Human Interferon α/β Receptor: Characterization and Molecular Cloning," *Cell* 77:391–400 (1994).

Novick, D., et al., "Soluble and Membrane–Anchored Forms of the Human IFN–α/β Receptor," *Journal of Leukocyte Biology* 57:712–718.

Constantinescu, S.N., et al., "Role of Interferon α/β Receptor Chain 1 in the Structure and Transmembrane Signaling of the Interferon α/β Receptor Complex," *Proc. Natl. Acad. Sci. USA* 91:9602–9606 (1994).

Colamonici, O.R., et al, "Characterization of Three Monoclonal Antibodies that Recognize the Interferon α2 Receptor," *Proc. Natl. Acad. Sci. USA* 87:7230–7234 (1990).

*Primary Examiner*—David L. Fitzgerald
*Attorney, Agent, or Firm*—Browdy and Neimark

[57] ABSTRACT

Antibodies directed against the ligand-binding component of the interferon (IFN)-α/β receptor (IFNα/βR, IFNAR2) are provided. The antibodies are capable of selectively modulating the activity of IFN-α as compared to IFN-β. By virtue of their selectivity, the antibodies are useful in clinical and analytical applications.

24 Claims, No Drawings

ANTIBODIES AGAINST THE INTERFERON (IFN) α/β RECEPTOR (IFNAR2) THAT PREFERENTIALLY BLOCK THE ACTIVITY OF IFN-α

FIELD OF THE INVENTION

The present invention relates to antibodies directed against the ligand-binding component of the interferon-α/β receptor which are capable of selectively modulating the activity of various Type I interferons.

EP publication No. 588,177 describes a soluble IFN-α receptor, having a molecular weight of about 40,000, which was identified by cross-linking with $^{125}$I-IFN-α2 and immunoprecipitation with anti-IFN-α monoclonal antibodies. When obtained from serum, this species had a molecular weight of 50K. It also describes the aforesaid 40,000 IFN-α binding protein, (hereinafter "IFNAB-BP" or ("IFNAB-BPII") obtained from urine in a homogenous state and having a sequence that differs from any other known protein. The IFNAB-BP binds to and blocks the activity of a variety of IFN-α subtypes, as well as the one of IFN-β.

EP publication No 676,413 describes cloning and sequencing of two cDNA molecules coding for precursors of IFNAB-BP. Both are probably derived from the same gene, e.g., by alternative splicing. Production of two recombinant proteins, designated IFNAB-BPI and IFNAB-BPII in mammalian and other host cells is also described. Polyclonal and monoclonal antibodies directed against IFNAB-BP and useful for blocking the IFN receptor, for immunoassays and immunopurification of IFNAB-BPI and IFNAB-BPII are also disclosed.

In the present invention there are described two groups of neutralizing antibodies made against IFNAB-BPII which bind to the Type I interferon receptor on human cells. One group of the antibodies is capable of blocking the activity of both IFN-α subtypes as well as the activity of IFN-β. Another group of antibodies is capable of selectively blocking the activity of various subtypes of interferon-α in human cells, without affecting the activity of interferon-β. Thus, one group of said antibodies may inhibit undesired effects of IFN-α with very little effect on the activity of IFN-β.

BACKGROUND OF THE INVENTION

Type I interferons (IFNs) (IFN-α IFN-β and IFN-ω) constitute a family of structurally related cytokines, usually defined by their ability to confer resistance to viral infections. Many other biological activities of type I IFNs have been reported, including inhibition of cell proliferation, induction of class I MHC antigens and several other immuno-regulatory activities (1). IFN-α and IFN-β are useful for the treatment of several viral diseases, including hepatitis-C (2,3) and viral warts (4,5), as well as certain malignancies such as hairy cell leukemia (6), chronic myelogenous leukemia (7) and Kaposi's sarcoma (8).

IFN-α was detected in sera of various patents having autoimmune diseases such as systemic lupus erythematosus (9), as well as AIDS patients (10). IFN-α was implicated in the progression of juvenile diabetes (11). Further, IFN-α therapy has been shown in some cases to lead to undesired side effects, including fever and neurological disorders (12). Hence there are pathological situations in which neutralization of IFN-α activity may be beneficial to the patient.

As in the case of other cytokines, IFN-α exerts its biological activities by binding to a cell surface receptor, which is specific for all IFN-α subtypes, as well as for IFN-β (13). A human IFN-α receptor (IFNAR) was identified and cloned from Daudi cells (14). The cloned receptor has a single transmembrane domain, an extracellular and an intracellular domain. When expressed in murine cells, this receptor confers responsiveness to human IFN-αB but not significantly to other IFN-α and IFN-β species, indicating that additional components may be involved in the response to IFN-β and to various IFN-α subtypes.

Several other studies indicate that there are additional components or receptor subunits involved in the binding of IFN-α and IFN-β (15–17). Nevertheless, it was reported that the already described receptor (14) is involved in binding of all IFN-α and IFN-β species (18). Indeed, a second receptor component, named IFN-α/β receptor was recently identified and cloned (EP publication No. 676,413 and ref. 19). We demonstrated that IFN-α/β receptor whose extracellular domain has the same sequence as IFNAB-BPI is the primary ligand-binding component of the Type I interferon receptor. Furthermore, interferon-α/β receptor and IFNAR cooperate in ligand-binding and form a ternary complex with Type I interferons on cell surface (20).

Monoclonal antibodies directed against IFNAR and capable of blocking the activity of Type I interferons in a non-selective manner were already described (21). Another monoclonal antibody, directed against an unidentified receptor component was described. This antibody blocked the activity of Type I interferons in a non-selective manner (22).

SUMMARY OF THE INVENTION

The present invention provides monoclonal antibodies directed against the IFN-α/β receptor which is the common receptor for IFN-α and IFN-β. These antibodies bind to several forms of the receptor which are either expressed on human cells or as the soluble forms IFNAB-BPI and IFNAB-BPII. Two types of neutralizing monoclonal antibodies were developed. One type exhibits a high titer when used for blocking of the antiviral activity of both IFN-α and IFN-β. The second type surprisingly shows a high blocking titer only with respect to the antiviral activity of IFN-α, while having a very low titer with respect to the activity of IFN-62 . Thus the unexpected second type of monoclonal antibodies may be used at a certain range of concentration for selectively blocking the activity of IFN-α while the activity of IFN-β will not be affected.

The present invention also provides humanized monoclonal antibodies directed against the IFN-α/β receptor expressed on human cells, IFNAB-BPI and IFNAB-BPII. Humanized monoclonal antibodies are mouse-human hybrid antibody molecules in which the variable domains are derived from the mouse antibody while the constant domains are of human origin.

The present invention also provides DNA molecules encoding the monoclonal antibodies and the humanized monoclonal antibodies directed against the IFN-α/β receptor, IFNAB-BPI and IFNAB-BPII.

The invention further provides replicable expression vehicles containing said DNA molecules, hosts transformed therewith and proteins produced by such transformed hosts. The term "DNA molecules" includes genomic DNA, cDNA, synthetic DNA and combinations thereof.

The invention also relates to DNA molecules which hybridize under stringent conditions to the above DNA molecules and encode proteins having the same biological activity as the monoclonal antibodies and humanized monoclonal antibodies directed against the IFN-α/β receptor, IFNAB-BPI and IFNAB-BPII.

The present invention also provides methods for preparation of host cells capable of production of functional monoclonal antibodies and humanized monoclonal antibodies directed against the IFN-α/β receptor, IFNAB-BPI and IFNAB-BPII.

The monoclonal antibodies according to the present invention inhibit the biological activity of human interferon-α in human cells without affecting the biological activity of human interferon-β. The biological activity was determined by quantitative evaluation of the inhibitory effect of the antibody when tested in a cytopathic effect inhibition assay, using human WISH cells and vesicular stomatitis virus.

DETAILED DESCRIPTION OF THE INVENTION

According to Israeli Patent Application No. 106591, an IFN-α/β binding protein having a molecular weight of 40,000 (IFNAB-BP) was isolated from normal urine by two chromatographic steps. Crude urinary proteins were loaded on a column consisting of IFN-α2 bound to agrose. The column was washed to remove non-relevant proteins and the bound proteins were then eluted at low pH. Eluted proteins were then resolved by size exclusion HPLC to give several protein peaks, one of which was characterized by its ability to react specifically with $^{125}$I-IFN-α2 and to block the antiviral activity of IFN-α and IFN-β. This protein was further characterized by N-terminal microsequence analysis. The resulting sequence was compared with and found different from that of the known IFNAR receptor (14). It was also different from any other known protein and it was not coded by any known DNA sequence, as determined by comparing it to Swissprot and Genebank data libraries, using the FastA program (23).

Homogenous preparations of urinary IFNAB-BP were used as an immunogen for preparation of antibodies.

The term "antibody" is meant to include polyclonal antibodies, monoclonal antibodies (Mabs), chimeric antibodies, anti-idiotypic (anti-Id) antibodies to antibodies that can be labeled in soluble or bound form, well as active fractions thereof provided by any known technique, such as, but not limited to enzymatic cleavage, peptide synthesis or recombinant techniques.

Polyclonal antibodies are heterogeneous populations of antibody molecules derived from the sera of animals immunizes with an antigen. A monoclonal antibody contains a substantially homogeneous population of antibodies specific to antigens, which population contains substantially similar epitope binding sites. Mabs may be obtained by methods known to those skilled in the art. See, for example Kohler and Milstein, *Nature* 256:495–497 (1975); U.S. Pat. No. 4,376,110; Ausubel et al, eds., *Current Protocols in Molecular Biology*, Greene Publishing Assoc. and Wiley Interscience, N.Y., (1987–1999); Harlow and Lane, *ANTIBODIES: A LABORATORY MANUAL*, Cold Spring Harbor Laboratory (1988); and Colligan et al., eds., *Current Protocols in Immunology*, Greene Publishing Assoc. and Wiley Interscience, N.Y., (1992–1996), the contents of which references are incorporated entirely herein by reference. Such antibodies may be of any immunoglobulin class including IgG, IgM, IgE, IgA, GILD and any subclass thereof. A hybridoma producing a Mab of the present invention may be cultivated in vitro, in situ or in vivo. Production of high titers of Mabs in vivo or in situ makes this the presently preferred method of production.

Chimeric antibodies are molecules different portions of which are derived from different animal species, such as those having the variable region derived from a murine Mab and a human immunoglobulin constant region. Chimeric antibodies are primarily used to reduce immunogenicity in application and to increase yields in production, for example, where murine Mabs have higher yields from hybridomas but higher immunogenicity in humans, such that human/murine chimeric Mabs are used. Chimeric antibodies and methods for their production are known in the art (Cabilly et al, *Proc. Natl. Acad. Sci. USA* 81:3273–3:277 (1984); Morrison et al., *Proc. Natl. Acad. Sci. USA* 81:6851–6855 (1984), Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication, WO 9702671 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the Mab with the Mab to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original Mab which induced the anti-Id. Thus, by using antibodies to the idiotypic determinants of a Mab, it is possible to identify other clones expressing antibodies of identical specificity.

Accordingly, Mabs generated against IFNAB-BPI, IFNAB-BPII, and related proteins of the present invention may be used to induce anti-Id antibodies in suitable animals, such as BALB/c mice. Spleen cells from such immunized mice are used to produce anti-Id hybridomas secreting anti-Id Mats. Further, the anti-Id Mabs can be coupled to a carrier such as keyhole limpet hemocyanin (KLH) and used to immunize additional BALB/c mice. Sera from these mice will contain anti-anti-Id antibodies that have the binding properties of the original Mab specific for an IFNAB-BPI or IFNAB-BPII epitope.

The anti-Id Mabs thus have their own idiotypic epitopes, or "idiotopes" structurally similar to the epitope being evaluated, such as IFNAB-BPI or IFNAB-BPII.

The term "antibody" is also meant to include both intact molecules as well as active fractions thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for selective blocking of the biological activity of IFN-α according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used for blocking the biological activity of IFN-α subtypes with little effect on the activity of interferon-β.

The present invention also provides DNA molecules encoding any of the antibodies of the present invention as defined above, replicable expression vehicles comprising any such DNA molecules, host cells transformed with any such expression vehicles including prokaryotic and eukaryotic and host cells.

The invention also includes a process for the production of any of the antibodies of the present invention by culturing hybridomas in accordance with the present invention and recovering the secreted monoclonal antibody.

The invention also includes a process for the production of any of the antibodies of the present invention by culturing transformed cells in accord with present invention and recovering the secreted antibody encoded by the DNA molecule and the expression vehicle within such transformed host cell.

The invention further relates to active muteins and active fractions of said antibodies and to fused proteins consisting of wild type antibodies, or their active muteins or their active fractions, fused to another polypeptide or protein and exhibiting a similar ability to block the biological activities of Type I IFNs.

DNA encoding said antibodies, their active fractions, muteins or fused proteins, and the operably linked transcriptional and translational regulatory signals, are inserted into eukaryotic vectors which are capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototrophy to an auxotropic host, biocide resistance, e.g., antibiotics, or resistance to heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals (24).

For the purposes of expression of said antibodies, their active fractions or derivatives, the DNA molecule to be introduced into the cells of choice will preferably be incorporated into a plasmid or viral vector capable of autonomous replication in the recipient host.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli*, for example, pBR322, ColE1, pSC101, pACYC 184, etc. (25); Bacillus plasmids such as pC194, pC221, pT127, etc. (26); Streptomyces plasmids including pIJ101 (27), Streptomyces bacteriophages such as IC31 (28) and Pseudomonas plasmids (29,30).

Preferred eukaryotic plasmids include BPV, vaccinia, SV40, 2-micron circle, etc., or their derivatives. Such plasmids are well known in the art (31–35).

Once the vector or DNA sequence containing the construct(s) has been prepared for expression, the expression vector may be introduced into an appropriate host cell by any of a variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 3153), *E. coli* W3110 (F$^-$, lambda$^-$, phototropic (ATCC 27325)), and other enterobackteria such as *Salmonella typhimurium* or *Serratia marcescens* and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and Chinese hamster ovary (CHO) cells, because they provide post-translational modifications to protein molecules including correct folding, correct disulfide bond formation, as well as glycosylation at correct sites. Also yeast cells and insect cells can carry out post-translational peptide modifications including high mannose glycosylation. A number of recombinant DNA strategies exist which utilize strong promoter sequences and high copy number of plasmids, which can be utilized for production of the desired proteins in yeast and in insect cells. Yeast cells recognize leader sequences on cloned mammalian gene products and secrete peptides bearing leader sequences. After the introduction of the vector, the host cells are grown in a selective medium, which selects for the growth of vector-containing cells. Expression of the cloned gene sequence(s) results in the production of said antibodies, fusion proteins, or muteins or active fractions thereof. The expressed antibodies are then isolated and purified by any conventional procedure involving extraction, precipitation, chromatography, electrophoresis, or the like, or by affinity chromatography.

As used herein the term "muteins" refers to analogs of said antibodies, in which one or more of the amino acid residues of said antibodies or their active fractions are replaced by different amino acid residues, or are deleted, or one or more amino acid residues are added to the original sequence of said antibodies without changing considerably the activity of the resulting products as compared with wild type antibodies or their active fractions. These muteins are prepared by known synthesis and/or by site-directed mutagenesis techniques, or any other known technique suitable therefor.

Any such mutein preferably has a sequence of amino acids sufficiently duplicative of those of said antibodies such as to have substantially similar activity to said antibodies or their active fractions. One group of said antibodies is capable of blocking the antiviral activity of human IFN-α2 and human IFN-β. Another group of said antibodies is capable of blocking the antiviral activity of human IFN-α2 while the activity of human IFN-β remains largely intact. Thus, it can be determined whether any given mutein has substantially the same activity as said antibody by means of routine experimentation comprising subjecting such a mutein, e.g., to a simple antiviral assay, as a mutein which blocks any species of type I interferon retains sufficient activity of said antibodies and therefore has at least one of the disclosed utilities of said antibodies and thus has substantially similar activity thereto.

In a preferred embodiment, any such mutein has at least 40% identity or homology with the sequence of one of the said antibodies. More preferably, it has at least 50%, at least 60%, at least 70%, at least 80% or, most preferably, at least 90% identity or homology thereto.

Muteins of said antibodies or their active fractions which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978, and Creighton, T. E., Proteins: Structure and Molecular Properties, W.H. Freeman & Co., San Francisco, 1983, which are hereby incorporated by reference. For a presentation of nucleotide sequence substitutions, such as codon preferences, see Ausubel et al, supra, at §§A.1.1–A.1.24, and Sambrook et al, supra, at Appendices C and D.

Preferred changes for muteins in accordance with the present invention are what are known as "conservative" substitutions. Conservative amino acid substitutions of said antibodies, polypeptides or protein or their active fractions may include synonymous amino acids within a group which have sufficiently similar physicochemical properties that substitution between members of the group will preserve the biological function of the molecule, Grantham, *Science*, Vol. 185, pp. 862–864 (1) is clear thatinsertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", *Science*, Vol. 181, pp. 223–230 (1973). Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acids | Synonymous Group |
|---|---|
| Ser | Ser |
| Arg | Arg |
| Leu | Leu Ile, Met |
| Pro | Pro |
| Thr | Thr |
| Ala | Ala |

TABLE III-continued

Most Preferred Groups of Synonymous Amino Acids

| Amino Acids | Synonymous Group |
|---|---|
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of said antibodies or their active fractions for use in the present invention include any known method steps, such as presented in U.S. Pat. Nos. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any mutein of said antibodies or their active fractions has an amino acid sequence essentially corresponding to that of said antibodies. The term "essentially corresponding to" is intended to comprehend proteins with minor changes to the sequence of the natural protein which do not affect the basic characteristics of the natural proteins, particularly insofar as their ability to block completely or selectively the activity of IFN-α and IFN-β is concerned. The type of changes which are generally considered to fall within the "essentially corresponding to" language are those which would result from conventional mutagenesis techniques of the. DNA encoding these antibodies, resulting in a few minor modifications, and screening for the desired activity in the manner discussed above.

Muteins in accordance with the present invention include proteins encoded by a nucleic acid, such as DNA or RNA, which hybridizes to DNA or RNA which encodes said antibodies in accordance with the present invention, under stringent conditions. The invention also includes such nucleic acid which is also useful as a probe in identification and purification of the desired nucleic acid. Furthermore, such nucleic acid would be a prime candidate to determine whether it encodes a polypeptide which retains the functional activity of said antibodies of the present invention. The term "stringent conditions" refers to hybridization and subsequent washing conditions which those of ordinary skill in the art conventionally refer to as "stringent". See Ausubel et al., *Current Protocols in Molecular Biology*, supra, Interscience, NY, §§6.3 and 6.4 (1987, 1992), and Sambrook et al., supra. Without limitation, examples of stringent conditions include washing conditions 12–20° C. below the calculated Tm of the hybrid under study in, e.g., 2*SSC and 0.5% SDS for 5 minutes, 2*SSC and 0.1% SDS for 15 minutes; 0.1*SSC and 0.5% SDS at 37° C. for 30–60 minutes and then a 0.1*SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See Ausubel, supra.

The term "fused protein" refers to a polypeptide comprising said antibodies or their active fractions or a mutein thereof, fused with another protein which, e.g., has an extended residence time in body fluids. Said antibodies or their active fractions may thus be fused to another protein, polypeptide or the like.

The term "salts" herein refers to both salts of carboxyl groups and to acid addition salts of amino groups of said antibodies, their active fractions, muteins, or fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to said antibodies or their active fractions.

"Functional derivatives" as used herein cover derivatives of said antibodies or their active fractions and their muteins and fused proteins, which may be prepared from the functional groups which occur as side chains on the residues or the N- or C-terminal groups, by means known in the art, and are included in the invention as long as they remain pharmaceutically acceptable, i.e., they do not destroy the activity of the protein which is substantially similar to the activity of said antibodies, and do not confer toxic properties on compositions containing it. These derivatives may, for example, include polyethylene glycol side-chains which may mask antigenic sites and extend the residence of said antibodies or their active fractions in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g., alkanoyl or carbocyclic aroyl groups) or O-acyl derivatives of free hydroxyl groups (for example that of seryl or threonyl residues) formed with acyl moieties.

As "active fractions" of said antibodies, muteins and fused proteins, the present invention covers any fragment or precursors of the polypeptide chain of said antibodies, or fused proteins containing any such fragment of said antibodies, alone or together with associated molecules or residues linked thereto, e.g., sugar or phosphate residues, or aggregates of any of the above antibodies, provided said fraction has substantially similar activity to said antibodies.

The present invention further relates to pharmaceutical compositions comprising a pharmaceutically acceptable carrier and the antibodies of the invention or their active muteins, fused proteins and their salts, functional derivatives or active fractions thereof.

The pharmaceutical compositions of the invention are prepared for administration by mixing said antibodies or their derivatives, with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

Said antibodies are useful for modulating or blocking the biological activities of various IFN-α subtypes for example in type I diabetes, various autoimmune diseases, graft rejections, AIDS and similar diseases, in which there is an aberrant expression of IFN-α i.e., said antibodies may be used in any condition where an excess of IFN-α is endogenously produced or exogenously administered.

Accordingly, said antibodies, humanized antibodies, their active fractions, muteins, fused proteins and their salts, functional derivatives, and active fractions thereof are indicated for the treatment of autoimmune diseases, for other inflammations in mammals, for treatments of toxicity caused by administration of interferon alpha or interferon beta, for juvenile diabetes, for lupus erythematosus and for AIDS.

The invention will now be illustrated by the following non-limiting examples:

EXAMPLE 1

Immunization of Mice With IFNAB-BP and Fusion With Myeloma Cells

Female Balb/C mice (3 months old) were first injected with 2 μg purified IFNAB-BP in an emulsion of complete Freund's adjuvant, and three weeks later, subcutaneously in incomplete Freund's adjuvant. Five additional injections were given at 10 day intervals, subcutaneously in PBS. Sera of these mice had binding titer 1:100,000 as determined by IsRIA (see below). The antisera blocked the antiviral activity of both IFN-α and IFN-β as determined by the following procedure: Pre-formed monolayers of human WISH cells in 96 well plates were incubated for 2 hr at 37° C. with twofold dilutions of antiserum (or monoclonal antibody). IFN-α2 or IFN-β (10 U/ml final; calibrated against NIH standards) was then added to all wells and the plates were further incubated for 4 hr. The cells were then challenged with vesicular stomatitis virus (VSV) and incubated overnight until a complete cytopathic effect was noticed in control wells lacking IFN. The neutralizing titer of the antibodies in wells showing 50% CPE was taken as, 9 units/ml. Hence, 1 blocking unit/ml is the antibody concentration needed for blocking the activity of 1 U/ml of IFN under these assay conditions. The serum of the immunized mice had a neutralizing titer of 120,000 U/ml for both IFN-α2 and IFN-β.

Final boosts of purified IFNAB-BP were then given intraperitoneally 4 and 3 days before the fusion. Fusion was performed using NSO/1 myeloma cell line and lymphocytes prepared from both the spleen and lymph nodes of the immunized mouse as fusion partners. The fused cells were distributed into 96 well plates and the hybridomas were selected in DMEM supplemented with HAT and 15% horse serum.

EXAMPLE 2

Screening of Hybridomas and Characterization of Monoclonal Antibodies

The screening of hybridomas producing anti-IFNAB-BP monoclonal antibodies was performed as follows: Hybridoma supernatant were tested for the presence of anti-IFNAB-BP antibodies by an inverted solid phase radioimmunoassay (sRIA) as follows. PVC microtiter plates (Dynatech Laboratories, Alexandria, Va.) were coated with affinity purified goat anti-mouse serum F(ab)2 antibodies (Jackson Labs, U.S.A.) (10 μg/ml, 100 μl/well). Following overnight incubation at 4° C. the plates were washed twice with PBS containing BSA (0.5%) and Tween 20 (0.05%) and blocked in washing solution for at least 2 hr at 37° C., Hybridoma culture supernatants (100 μl/well) were added and the plates were incubated for 4 hr at 37° C. The plates were then washed three times with the washing solution and $^{125}$I-IFNAB-BP (100 μl, 105 cpm) was added for further incubation of 16 hr at 4° C. The plates were washed 3 times and individual wells were cut and counted in a gamma counter. Samples giving counts that were at least 5 times higher than the negative control value were considered positive (Table IV). All positives clones were selected and subcloned. Individual subclones were injected into Balb/C mice that had been primed with pristane for the production of ascites. Immunoglobulins were isolated from ascitic fluids by precipitation with ammonium sulfate (50% saturation). The isotypes of the antibodies were defined by using a commercially available ELISA kit (Amersham, UK).

The various monoclonal antibodies, either as hybridoma supernatants, concentrated hybridoma supernatants, ascitic fluids or immunoglobulins from ascitic fluids were further tested for their ability to block the receptor and prevent the antiviral activity of IFN-α2 and IFN-β as described above for the serum of immunized mice. The results are given in Table IV. Thus it was found that monoclonal antibodies 16.3, 53.2 and 392.1 block the antiviral activity of both IFN-α2 and IFN-β at comparable titers, whereas the titer of monoclonal antibodies 35.9, 51.44 and 234.14 against IFN-α2 was unexpectedly found to be significantly higher than their titer against IFN-β. Thus monoclonal antibodies 35.9, 51.44 and 234.14 may be used at a certain range of concentration for selectively blocking the activity of IFN-α while the activity of IFN-β will not be affected.

TABLE IV

Characterization of monoclonal antibodies to IFN-α/β receptor (IFNAB-BP)

| Antibody | IsRIA (cpm) | Neutralizing titer IFN-α2 (U/ml) | Neutralizing titer IFN-β (U/ml) | Ig class |
|---|---|---|---|---|
| 16.3 Hybridoma supernatant | 39,103 | >5,120 | ND | IgG1 |
| 16.3 Ascitic fluid[1] | ND[2] | 60,000 | 60,000 | IgG1 |
| 35.9 Hybridoma supernatant | 33,100 | 1,280 | 150 | IgG1 |
| 35.9 Ascitic fluid | ND | 60,000 | 15,000 | IgG1 |
| 51.44 Hybridoma supernatant | 6,345 | 1,000 | <75 | IgG2a |
| 51.44 Ig (5 mg/ml) | ND | 15,000 | <2500 | IgG2a |
| 53.2 Hybridoma supernatant | 26,737 | 2,000 | ND | IgG1 |
| 53.2 Ascitic fluid | ND | 120,000 | 70,000 | IgG1 |
| 117.7 Hybridoma supernatant | 38,945 | 2,000 | ND | IgG1 |
| 117.7 Ig (10 mg/ml) | ND | 28,800,000 | 2,000,000 | IgG1 |
| 234.14 Hybridoma supernatant | 21,812 | >5,120 | <200 | IgG2a |
| 234.14 Ig (10 mg/ml) | ND | 1,440,000 | 23,000 | IgG2a |
| 392.1 Hybridoma supernatant | 34,390 | 2,400 | ND | IgG1 |
| 392.1 Ascitic fluid | ND | 160,000 | 70,000 | IgG1 |

[1]about 5 mg/ml Ig.
[2]Not done.

EXAMPLE 3

Use of Monoclonal Antibodies for the ELISA Test of IFNAB-BPII

Microtiter plates (Dynatech or Maxisorb, bNunc) were coated with anti-IFNAB-BP monoclonal antibody overnight at 4° C. This first coating can be done with monoclonal antibody No. 46.10 (Ig fraction, 120 µl/well, 10 µg/ml in PBS). Monoclonal antibody No. 46.10 was described in EP Publication No. 676,413.

Alternatively, monoclonal antibody No. 117.7 may be used for the first coating. The plates were washed with PBS containing BSA (0.5%), Tween 20 (0.05%) and $NaN_3$ (0.02%) (Blocking Solution) and blocked in the same solution overnight at 37° C. The tested samples were serially diluted twofold (starting with 1:4) in the Blocking Solution containing 0.1% NP40 and 0.65 M NaCl and added to the wells (100 µl) for 4 hr. at 37° C. The plates were then washed 3 times with PBS containing 0.05% Tween 20 (PBS/Tween) followed by the addition of biotinylated monoclonal antibody No. 234.14 (1:1000 in Blocking Solution but without $NaN_3$, 100 µl/well) for further incubation overnight at 4° C. The plates were washed 3 times with PBS/Tween, (100 µl/well), and a conjugate of Streptavidin—horseradish peroxidase (Jackson Labs, 1:10, 000 in PBS/Tween, 100 µl/well) was added for 2 hr. at room temperature. The plates were washed 3 times with PBS/Tween and the color was developed by adding to each well 100 ml of a freshly prepared solution of ABTS (2,2'-azino-bis(3-ethylbenzthiazoline-6-sulfonic acid, Sigma, 10 mg; 6.4 ml $H_2O$; 2.2 ml of 0.2M $Na_2HPO_4$; 1.4 ml 0.2 M citric acid; 1 µl $H_2O_2$) as a substrate. Color develops by 30 min. and the reaction may be stopped by addition of 100 µl/well of 0.2 M citric acid. The plates were read by an automatic ELISA reader at 405 nm, correcting for non-specific reading at 630 nm. The lower limit of detection of this assay was 30 pg/ml.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

Hybridomas 46.10, 117.7 and 234.14 were deposited at the Pasteur Institute (CNCM), 28, Rue du Dr Roux, 75274 Paris Cédex 15, under deposit numbers I-1697, I-1698, and I-1699, respectively on Apr. 23, 1996.

REFERENCES

1. Taylor, J. L., et al., "Recent progress in interferon research: molecular mechanisms of regulation, action and virus circumvention", *Virus Research*, 15:1–26, 1990.

2. Bisceglie, A. M., et al., "Recombinant interferon alpha therapy for chronic hepatitis C. A randomized, double-bind, placebo-controlled trial", *New Eng. J. Med.*, 321: 1506–1510, 1989.

3. McDonnell, W. M., et al., "Acute hepatitis C infection: interferon finally succeeds", *Gastroenterology (US)*, 103: 1359–1360, 1992.

4. Friedman-Kien, A. E., et al., "Natural interferon alpha for treatment of condylomata acuminata", *J. Am. Med. Assn.*, 259: 533–5313, 1988.

5. Mains, J., et al., "Interferon: current and future clinical uses in infectious disease practice", *Int. J. Stud. AIDS*, 3:4–9, 1992.

6. Berman, E., et al., "Incidence of response and long term follow up in patients with hairy cell leukemia treated with recombinant interferon Alpha-2a", *Blood*, 75: 839–845, 1990.

7. Talpaz, M., et al., "Clinical investigation of human alpha interferon in chronic myelogenous leukemia", *Blood*, 69: 1280–1288, 1987.

8. De Wit, R., et al., "Clinical and virological effects of high-dose recombinant-interferon-a in disseminated AIDS-related Kaposi's sarcoma", *Lancet*, 2: 1214–1222, 1988.

9. Klippel, J. H., et al., "Serum alpha interferon and lymphocyte inclusions in systemic lupus erythematosus", *Annals of the Rheumatic Diseases*, 44: 104–108, 1985.

10. Lau, A. S., et al., "Regulation of tumor necrosis factor receptor expression by acid-labile interferon-alpha from AIDS sera", *AIDS Res. Hum. Retroviruses*, 7: 545–552, 1991.

11. Stewart, T. A., "Induction of type I diabetes by interferon-a in transgenic mice", *Science*, 260: 1942–1946, 1993.

12. Tsavaris, N., et al., "Treatment of renal cell carcinoma with escalating doses of alpha-interferon", *Chemotherapy (Switzerland)*, 39: 361–366, 1993.

13. Branka, A. A., et al., "Evidence that types I and II interferons have different receptors", *Nature*, 294: 768–770, 1981.

14. Uze, G., et al., "Genetic transfer of a functional human interferon a receptor into mouse cells: cloning and expression of its cDNA", *Cell*, 60: 225–234, 1990.

15. Colamonici, O. R., et al., "Characterization of three monoclonal antibodies that recognize the interferon-a2 receptor", *Proc. Natl. Acad. Sci. USA*, 87:7230–7234, 1990.

16. Platanias, L. C., et al., "Expression of the IFN-receptor in hairy cell leukemia", *Brit. J. Haematology*, 82: 541–546, 1992.

17. Colaminici, O. R., et al., "Identification of a novel subunit of the type I Interferon receptor localized to human chromosome 21", *J. Biol. Chem.*, 268: 10895–10899, 1993.

18. Benoit, P., et al., "A monoclonal antibody to recombinant human IFN-a receptor inhibits biologic activity of several species of human IFN-α IFN-β and IFN-omega", *J. Immunol.*, 150:707–716, 1993.

19. Novick, D., et al., "The Human Interferon/wbw receptor: Characterization and molecular cloning", *Cell*, 77: 391–400, 1994.

20. Cohen, B., et al., "Ligand-induced association of the Type I interferon receptor components", *Molec. Cell. Biol.*, 15: 4208–4214, 1995.

21. Benoit, P., et al., "A Monoclonal Antibody to Recombinant Human IFN-alpha Receptor Inhibits Biologic Activity of Several Species of Human IFN-alpha, IFN-beta, and IFN-omega—Detection of Heterogeneity of the Cellular Type-I IFN Receptor", *J. Immunol.*, 150(3): 707–716, 1993.

22. Colamonici, O. R., et al., "Identification of a Novel Subunit of the Type-I Interferon Receptor Localized to Human Chromosome-21", *J. Biol. Chem.*, 268(15): 10895–10899, 1993.

23. Pearson, W. R., et al., "Improved tools for biological sequence comparison", *Proc. Natl. Acad. Sci. USA*, 85: 2444–2448, 1988.

24. Okayama, H., et al., "A cDNA cloning vector that permits expression of cDNA inserts in mammalian cells", *Mol. Cell. Biol.*, 3: 280–289, 1983.

25. Maniatis, et al., *Molecular Cloning: A Laboratory Manual*, Cold Spring Harbor Laboratory, New York, 1982.

26. Gryczan, T., *The Molecular Biology of the Bacilli*, Academic Press, NY (1982), pp. 307–329.

27. Kendall, K. J. et al., *J. Bacteriol.*, 169: 4177–4183, 1987.

28. Chater, K. F., et al., in "Sixth International Symposium on Actinomycetales Biology", Akademiai Kaido, Budapest, Hungary (1986), pp. 45–54.

29. John, J. F., et al., (1986) *Rev. Infect. Dis.*, 8: 693–704.

30. Izaki, K., (1978) *Jpn. J. Bacteriol.*, 33: 729–742.

31. Botstein, D., et al., (1982) *Miami Wint. Symp.*, 19: 265–274.

32. Broach, J. R., in "The Molecular Biology of the Yeast Saccharomyces: Life Cycle and Inheritance", Cold Spring Harbor Laboratory, Cold Spring Harbor, N.Y., pp. 445–470, 1981.

33. Broach, J. R., (1982) *Cell*, 28:203–204.

34. Bollon, D. P., et al., (1980) *J. Clin. Hematol. Oncol.*, 10: 39–48.

35. Maniatis, T., in "Cell Biology: A Comprehensive Treatise, Vol. 3: Gene Expression", Academic Press, NY, pp. 563–608, 1980.

36. Mizushima, S., et al., "pEF-BOS, a powerful mammalian expression vector", *Nucleic Acid Res.*, 18: 5322–5328, 1990.

37. Byrn, R. A., et al., *Nature (London)*, 344: 667–670, 1990.

38. Frohman, M. A., et al., *Proc. Natl. Acad. Sci. USA*, 85: 8998–9002, 1988.

39. Graham, F. L., et al., *Virology*, 52: 456–467, 1973.

40. Munson, P. J., et al., *Anal. Biochem.*, 1137: 220–239, 1980.

What is claimed is:

1. An isolated polypeptide comprising the amino acid sequence of an antibody or a mutein of an antibody, wherein the antibody or mutein is other than a polyclonal antibody;

is capable of binding to the IFN-α/β receptor polypeptide and of blocking the biological activity of IFN-α and IFN-β; and exhibits a higher antiviral-blocking titer against IFN-α than against IFN-β;

or a salt or functional derivative thereof.

2. A polypeptide in accordance with claim 1, wherein said polypeptide is a monoclonal antibody.

3. A hybridoma which produces a monoclonal antibody according to claim 2.

4. A polypeptide in accordance with claim 1, wherein said polypeptide is a chimeric antibody.

5. A polypeptide in accordance with claim 1, wherein said polypeptide is a humanized antibody.

6. A polypeptide in accordance with claim 1, wherein said amino acid sequence is an active fraction of a monoclonal antibody or a mutein thereof.

7. An isolated DNA molecule comprising a segment encoding a polypeptide according to claim 1.

8. An isolated DNA molecule comprising a segment encoding a polypeptide according to claim 6.

9. A DNA in accordance with claim 7, wherein said DNA segment is operably linked to transcriptional and translational regulatory signals.

10. A DNA in accordance with claim 8, wherein said DNA segment is operably linked to transcriptional and translational regulatory signals.

11. A DNA in accordance with claim 7 which is an expression vector comprising said DNA segment.

12. A DNA in accordance with claim 8 which is an expression vector comprising said DNA segment.

13. A host cell capable of expressing a polypeptide that binds to the IFN-α/β receptor, wherein said host cell carries an expression vector in accordance with claim 11.

14. A host cell capable of expressing a polypeptide that binds to the IFN-α/β receptor, wherein said host cell carries an expression vector in accordance with claim 12.

15. A method of producing a polypeptide which binds to the IFN-α/β receptor comprising culturing a host cell in accordance with claim 13 and expressing the polypeptide encoded in said expression vector.

16. A method of producing a polypeptide which binds to the IFN-α/β receptor comprising culturing a host cell in accordance with claim 14 and expressing the polypeptide encoded in said expression vector.

17. A pharmaceutical composition for modulating or blocking the biological activity of IFN-α comprising the polypeptide of claim 1 and a pharmaceutically acceptable carrier.

18. A method of modulating or blocking the biological activity of IFN-α comprising administering an effective amount of the pharmaceutical composition of claim 17 to a subject in need thereof.

19. Monoclonal antibody 117.7 (CNCM I-1698).

20. Monoclonal antibody 234.14 (CNCM I-1699).

21. The hybridoma designated NUR 2 117.7 and deposited at the Pasteur Institute (CNCM) under accession no. I-1698.

22. The hybridoma designated NUR 2 234.14 and deposited at the Pasteur Institute (CNCM) under accession no. I-1699.

23. An immunoassay kit comprising;

(a) either monoclonal antibody 46.10 or monoclonal antibody 117.7 (CNCM I-1698), and (b) monoclonal antibody 234.14 (CNCM I-1699).

24. An immunoassay kit according to claim 23, further comprising a microtiter plate upon which said monoclonal antibodies are immobilized.

* * * * *

UNITED STATES PATENT AND TRADEMARK OFFICE
CERTIFICATE OF CORRECTION

PATENT NO. : 6,136,309
DATED : Oct. 24, 2000
INVENTOR(S) : Novick et al.

It is certified that error appears in the above-identified patent and that said Letters Patent is hereby corrected as shown below:

Cover page, line [73], delete "Italy" and insert therefor --Israel--.

Signed and Sealed this

Eighth Day of May, 2001

Attest:

NICHOLAS P. GODICI

Attesting Officer     Acting Director of the United States Patent and Trademark Office